(12) United States Patent
Hirata et al.

(10) Patent No.: US 12,262,905 B2
(45) Date of Patent: Apr. 1, 2025

(54) BENDING STRUCTURE AND JOINT FUNCTION PART

(71) Applicant: NHK SPRING CO., LTD, Yokohama (JP)

(72) Inventors: Takafumi Hirata, Yokohama (JP); Shimpei Kurokawa, Yokohama (JP); Yuki Hotoda, Yokohama (JP)

(73) Assignee: NHK Spring Co., Ltd., Yokohama (JP)

( * ) Notice: Subject to any disclaimer, the term of this patent is extended or adjusted under 35 U.S.C. 154(b) by 1051 days.

(21) Appl. No.: 17/268,929

(22) PCT Filed: Aug. 2, 2019

(86) PCT No.: PCT/JP2019/030599
§ 371 (c)(1),
(2) Date: Feb. 16, 2021

(87) PCT Pub. No.: WO2020/036085
PCT Pub. Date: Feb. 20, 2020

(65) Prior Publication Data
US 2023/0001590 A1    Jan. 5, 2023

(30) Foreign Application Priority Data

Aug. 14, 2018 (JP) .................................. 2018-152642
Feb. 4, 2019 (JP) .................................. 2019-017778

(51) Int. Cl.
A61B 17/29     (2006.01)
A61B 17/00     (2006.01)
(Continued)

(52) U.S. Cl.
CPC .......... *A61B 17/2909* (2013.01); *A61B 34/37* (2016.02); *B25J 3/00* (2013.01);
(Continued)

(58) Field of Classification Search
CPC .......... B25J 17/00; B25J 17/02; B25J 9/1075; A61B 34/70; A61B 17/29; A61B 34/30;
(Continued)

(56) References Cited

U.S. PATENT DOCUMENTS 5,271,543 A * 12/1993 Grant .................. A61B 17/115
227/19
5,405,073 A    4/1995 Porter
(Continued)

FOREIGN PATENT DOCUMENTS

DE         822 044 C      11/1951
EP         0 397 489 B1   7/1995
(Continued)

*Primary Examiner* — Pamela Rodriguez
(74) *Attorney, Agent, or Firm* — Norris McLaughlin, P.A.

(57) ABSTRACT

Provided is a bending structure and a joint function part, capable of ensuring sufficient flexibility and rigidity in an axial direction. The bending structure is provided with an outer coiled part formed of a wire wound in a coiled shape and an inner coiled part formed of a wire wound in a coiled shape and arranged in the outer coiled part, wherein the outer coiled part has a plurality of gaps to distance adjacent coils, and coils of the inner coiled part are provided so as to correspond to the gaps of the outer coiled part and fit between the adjacent coils while being in contact with the adjacent coils of the outer coiled part.

15 Claims, 13 Drawing Sheets

(51) Int. Cl.
*A61B 17/28* (2006.01)
*A61B 34/00* (2016.01)
*A61B 34/30* (2016.01)
*A61B 34/37* (2016.01)
*B25J 3/00* (2006.01)
*B25J 9/10* (2006.01)
*B25J 17/02* (2006.01)
*F16F 3/06* (2006.01)

(52) U.S. Cl.
CPC ............. *B25J 9/1075* (2013.01); *B25J 17/02* (2013.01); *F16F 3/06* (2013.01); *A61B 2017/00305* (2013.01); *A61B 17/28* (2013.01); *A61B 2017/2905* (2013.01); *A61B 2017/2908* (2013.01); *A61B 2017/2918* (2013.01); *A61B 2017/292* (2013.01); *A61B 2017/2939* (2013.01); *A61B 2034/301* (2016.02); *A61B 34/70* (2016.02)

(58) Field of Classification Search
CPC .................. A61B 34/71; A61B 17/28; A61B 2017/00305; A61B 2034/305; A61B 2017/2939; A61B 34/37; A61B 2034/301; A61B 2017/2918; A61B 2017/292; A61B 2017/2905; A61B 2017/2908; F16F 3/06
See application file for complete search history.

(56) References Cited

U.S. PATENT DOCUMENTS

| | | | |
|---|---|---|---|
| 5,465,894 | A | 11/1995 | Clark et al. |
| 5,448,989 | A | 12/1995 | Heckele |
| 5,851,212 | A | 12/1998 | Zirps et al. |
| 5,904,647 | A | 5/1999 | Ouchi |
| 8,105,350 | B2 | 1/2012 | Lee et al. |
| 2009/0240274 | A1 | 9/2009 | Boebel et al. |
| 2009/0247820 | A1 | 10/2009 | Nomura et al. |
| 2011/0144656 | A1 | 6/2011 | Lee et al. |
| 2011/0152880 | A1 | 6/2011 | Alvarez et al. |
| 2012/0253324 | A1 | 10/2012 | Lee et al. |

FOREIGN PATENT DOCUMENTS

| | | | | |
|---|---|---|---|---|
| JP | 7-410 | A | | 1/1995 |
| JP | 7-213526 | A | | 8/1995 |
| JP | 7-265323 | A | | 10/1995 |
| JP | 10-165361 | A | | 6/1998 |
| JP | 2008-178656 | A | * | 8/2008 |
| JP | 2009-240774 | A | | 10/2009 |
| JP | 2009-538186 | A | | 11/2009 |
| JP | 2011-177231 | A | | 9/2011 |

* cited by examiner

BENDING STRUCTURE AND JOINT FUNCTION PART

FIELD OF THE INVENTION

The present invention relates to a bending structure used for a joint function part of a robot or the like and a joint function part using the bending structure.

BACKGROUND OF THE INVENTION

Robots, manipulators, actuators or the like in various fields may have joint function parts. As a bending structure applied to such a joint function part, there is a flexible member disclosed in Patent document 1, for example.

The flexible member of Patent document 1 is configured by swingably engaging a plurality of disc elements with each other to perform bending operation as a whole according to swinging of each disc element.

The flexible member having the structure smoothly performs the bending operation and assures rigidity against compression in an axial direction, to stabilize the bending operation.

The flexible member of Patent document 1, however, has a problem that the structure is complicated because the plurality of disc elements are engaged with each other.

PATENT DOCUMENT 1: JP 2009-538186 A

SUMMARY OF THE INVENTION

A problem to be solved is that a structure is complicated if bending operation is stabilized.

In order to simplify structure while stabilizing bending operation, the present invention mainly characterizes a bending structure being bendable with respect to an axial direction by comprising an outer coiled part formed of a wire which is wound in a coiled shape to have a plurality of coils in the axial direction, and an inner coiled part formed of a wire which is wound in a coiled shape to have a plurality of coils in the axial direction and arranged in the outer coiled part, wherein the outer coiled part has a plurality of gaps to distance adjacent coils in the axial direction, and the coils of the inner coiled part are provided so as to correspond to the gaps of the outer coiled part and fit between the adjacent coils while being in contact with the adjacent coils of the outer coiled part.

Further, the present invention mainly characterizes a joint function part to which the aforementioned bending structure is applied by comprising a base part and a movable part configured to displace relatively to the base part, wherein the bending structure is provided between the base part and the movable part to bend according to displacement of the movable part relative to the base part.

According to the present invention, since the bending structure is configured by arranging the inner coiled part in the outer coiled part, the structure is simplified.

Further, since the coils of the inner coiled part fit between the adjacent coils while being in contact with the adjacent coils of the outer coiled part, rigidity in the axial direction is ensured.

Furthermore, at the time of the bending, the gaps of the outer coiled part are reduced on an inner side of the bending to displace the inner coiled part toward an outer side of the bending, and the gaps of the outer coiled part are enlarged on an outer side of the bending to allow the displacement of the inner coiled part, thereby to ensure sufficient flexibility even while the rigidity in the axial direction is ensured.

As a result, the present invention enables the structure to be simplified while stabilizing the bending operation.

Moreover, in the present invention, since the gaps of the outer coiled part are reduced on the inner side of the bending and the gaps of the outer coiled part are enlarged on the outer side of the bending, the length on the axis of the outer coiled part is not changed by comparison with a straight state. If it is used to guide a flexible member movably in the axial direction on an inner peripheral side, a moving amount of the flexible member is certainly kept constant.

BRIEF DESCRIPTION OF THE DRAWINGS

FIGS. 5A and 5B are schematic sectional views illustrating a drop-off of an inner coiled part from an outer coiled part in which FIG. 5A is a state before the drop-off and FIG. 5B is a state after the drop-off;

EMBODIMENT FOR CARRYING OUT THE INVENTION

The object that a structure is simplified while bending operation is stabilized is accomplished by a bending structure having a double coil shape in which an inner coiled part is arranged in an outer coiled part.

Namely, the bending structure is a bending structure being bendable with respect to an axial direction, comprising an outer coiled part formed of a wire which is wound in a coiled shape to have a plurality of coils in the axial direction, and an inner coiled part formed of a wire which is wound in a coiled shape to have a plurality of coils in the axial direction and arranged in the outer coiled part.

The outer coiled part has a plurality of gaps to distance adjacent coils in the axial direction, and the coils of the inner coiled part are provided so as to correspond to the gaps of the outer coiled part and fit between the adjacent coils while being in contact with the adjacent coils of the outer coiled part.

The outer coiled part may have the gaps in respective interspaces of the adjacent coils in the axial direction, but may be configured to have the gaps only in part in the axial direction.

A movable length in which the inner coiled part is movable in a diametral direction relatively to an axis of the outer coiled part may be equal to or less than half of (a diameter of the outer coiled part–a diameter of the inner coiled part).

In this case, it may be configured to have a restricting member to restrict movement of the inner coiled part so that the movable length is equal to or less than half of (the diameter of the outer coiled part–the diameter of the inner coiled part).

The restricting member may be a flexible member and the bending structure may be configured to pass the flexible member movably in the axial direction and to be bendable as well as the flexible member.

Further, the inner coiled part and the outer coiled part may be formed separately. In a case that the inner coiled part and the outer coiled part are formed separately, the inner coiled part may be screwed into the outer coiled part.

A joint function part to which the bending structure for the flexible member may comprise a base part and a movable part configured to displace relatively to the base part. In this case, the bending structure is provided between the base part and the movable part to bend according to displacement of the movable part relative to the base part.

Further, the joint function part may have a flexible tube being interposed between the base part and the movable part and being extendable and compressible in the axial direction. In this case, the bending structure is arranged along an axial center portion of the flexible tube in the axial direction.

Figure 1:
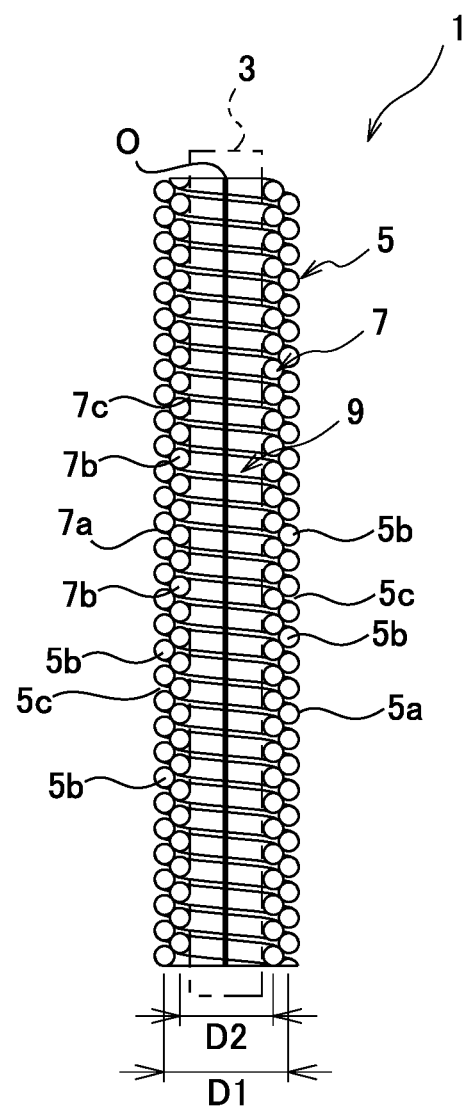
FIG. 1 is a sectional view illustrating a bending structure according to an embodiment 1 of the present invention.
Figure 2:
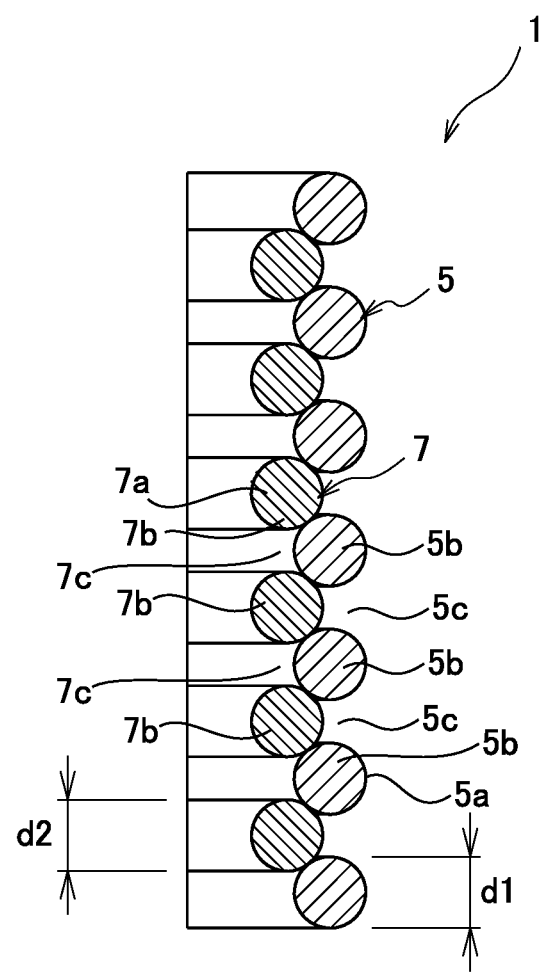
FIG. 2 is an enlarged view illustrating a part of the bending structure of FIG. 1.

FIG. 1 is a sectional view illustrating a bending structure for a flexible member according to the embodiment 1 of the present invention, and FIG. 2 is an enlarged view partly illustrating the same.

A bending structure 1 is one applied to a joint function part for, for example, robots, manipulators, actuators and the like in various fields. The bending structure 1 is provided between a base part and a movable part of the joint function part, and supports the movable part displaceably with respect to the base according to bending.

The bending structure 1 of the present embodiment has a double coil shape, and is provided with an outer coiled part 5, and an inner coiled part 7. With the double coil shape, the bending structure 1 of the present embodiment is bendable relatively to an axial direction, has a length of a central axis or axis O in the axial direction is approximately constant before, after and during bending based on that an inner diametral side of the bending is compressed and an outer diametral side of the bending is extended when the bending is performed according to external force, and restricts compression in the axial direction when the bending is not performed or the like. The bending structure 1 of the present embodiment is also provided with a flexible member 3 serving as a restricting member.

The flexible member 3 passes through the bending structure 1 being movably in the axial direction, and restricts deviation of the inner and the outer coiled parts 5, 7 in a diametral direction although the details will be explained later. The flexible member 3 of the present embodiment is configured by using, for example, a push-pull cable or the like. According to this, the bending structure 1 has a function to guide the flexible member 3 in the axial direction, and is bendable as well as the flexible member 3 according to bending operation of the joint function part.

It should be noted that the bending means that the axis O of the joint function part or the bending structure 1 is curved or bent. Further, the flexible member 3 may be omitted.

The outer coiled part 5 is a coil spring, and is made of a wire 5a would in a coiled shape. The outer coiled part 5, therefore, has a plurality of coils 5b in the axial direction. It should be noted that the coil 5b means one turn for composing the coiled shape (the same applies to the following).

The material of the wire 5a may be metal, resin or the like. The sectional shape of the wire 5a is formed into a circular shape, but may be oval or the like.

A mean diameter D1 of the outer coiled part 5 is constant from one end to the other end in the axial direction. The mean diameter D1 of the outer coiled part 5 may be, however, varied in the axial direction.

The outer coiled part 5 has a plurality of gaps 5c to axially distance adjacent coils 5b in the axial direction. The gaps 5c of the present embodiment are formed in respective interspaces of the adjacent coils 5c in the axial direction, and all the gaps 5c have the same dimension in the axial direction. The gaps 5c may be, however, provided in only some interspaces between the coils 5c in the axial direction. Further, the dimensions of the gaps 5c in the axial direction may be varied.

The inner coiled part 7 is a coil spring, and is made of a wire 7a would in a coiled shape having a plurality of coils 7b in the axial direction. In the inner coiled part 7, in the same way as the outer coiled part, the material of the wire 7a may be metal, resin or the like, and the sectional shape of the wire 7a is formed into a circular shape, but may be oval or the like.

The inner coiled part 7 is arranged inside the outer coiled part 5, and defines a passing portion 9 through which the flexible member 3 is passed on the inner circumference. The inner coiled part 7 of the present embodiment is screwed into the outer coiled part 5. With this screwing, the coils 7b of the inner coiled part 7 are arranged in the respective interspaces of the adjacent coils 5b of the outer coiled part 5. The inner coiled part 7 has, therefore, a structure in which the coils 7b are provided so as to correspond to the gaps 5c of the outer coiled part 5.

Further, the coils 7b of the inner coiled part 7 fit between the adjacent coils 5b while being in contact with the adjacent coils 5b of the outer coiled part 5 according to settings of a mean diameter D2 and a wire diameter d2 of the wire 7a.

In addition, the mean diameter D2 of the inner coiled part 7 is constant from one end to the other end in the axial direction. The mean diameter D2 of the inner coiled part 7 may be, however, varied in the axial direction according to the mean diameter D1 of the outer coiled part 5 or the like.

Further, the wire diameter d2 of the wire 7a is the same as the wire diameter d1 of the wire 5a of the outer coiled part 5. The wire diameter d2 of the wire 7a may be, however, greater or less than the wire diameter d1 of the wire 5a of the outer coiled part 5.

The inner coiled part 7 has a plurality of gaps 7c to distance adjacent coils 7b in the axial direction. The gaps 7c are formed in respective interspaces of the adjacent coils 7c in the axial direction according to the screwing into the outer coiled part 5, and all the gaps 7c have the same dimension in the axial direction.

It should be noted that the outer coiled part 5 and the inner coiled part 7 may have, other than the structure having the gaps 5c, 7c in the respective interspaces between the adjacent coils 5b, 7b in a free state in which the inner coiled part 7 is not arranged in the outer coiled part 5, a structure (close contact spring) in which the adjacent coils 5b, 7b are closely contact with each other in the free state. Further, only one of the outer coiled part 5 and the inner coiled part 7 may be the close contact spring.

In a case that the outer coiled part 5 and the inner coiled part 7 are the close contact springs in the free state, the inner coiled part 7 and the outer coiled part 5 are screwed together, thereby to mutually distance the interspaces between the coils 5b, 7b and form the gaps 5c of the outer coiled part 5 and the gaps 7c of the inner coiled part 7. In this case, initial tension may be applied to the bending structure 1 having the double coil shape.

Figure 3:
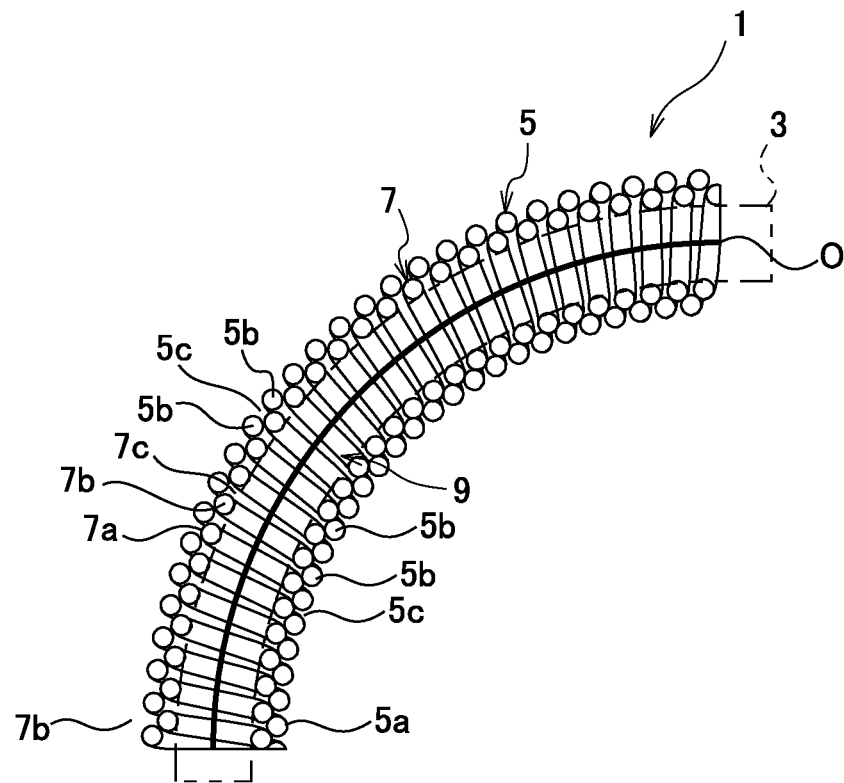
FIG. 3 is a sectional view illustrating a bending state of the bending structure of FIG. 1.
Figure 4:
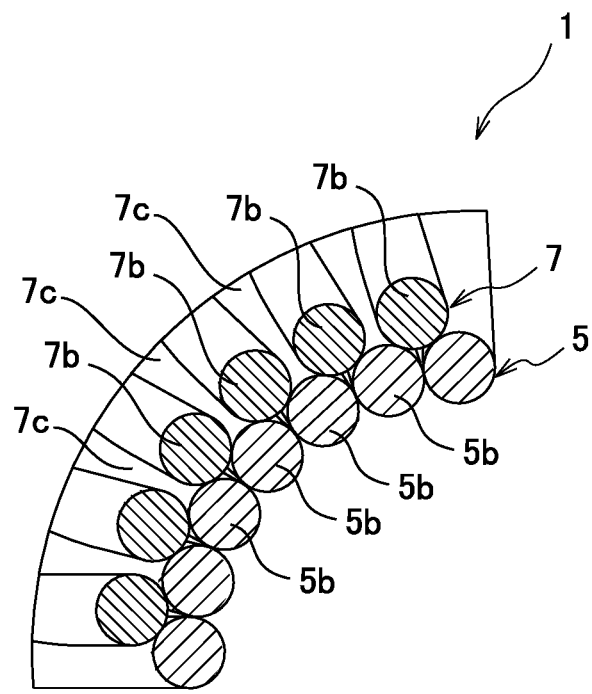
FIG. 4 is an enlarged view illustrating a part of the bending structure of FIG. 3.

FIG. 3 is a sectional view illustrating a bending state of the bending structure of FIG. 1, and FIG. 4 is an enlarged view partly illustrating the same.

In the bending structure 1, as illustrated in FIGS. 1 and 2, the coils 7b of the inner coiled part 7 fit between the adjacent coils 5b while being in contact with the adjacent coils 5b of the outer coiled part 5 when the axis O (being also the axis of the outer coiled part 5) is in a straight state without bending.

Accordingly, the bending structure 1 prevents, by the coils 7b of the inner coiled part 7, the gaps 5c of the outer coiled part 5 from being compressed to be prevented from being compressed as a whole even if compressive force acts in the axial direction. It should be noted that the gaps 7c of the inner coiled part 7 are prevented by the coils 5b of the outer coiled part 5 from being compressed if the inner coiled part 7 is as a basis.

The bending structure 1, therefore, prevents compression of itself and the joint function part to which the bending structure is applied. As a result, when guiding movement of the flexible member 3 in the axial direction, the length of the axis O and a moving amount of the flexible member 3 passing on the axis O are kept constant to also ensure stability of operation of the flexible tube 3.

As illustrated in FIGS. 3 and 4, when the axis O of the bending structure 1 is bent, the gaps 5c of the outer coiled part 5 are reduced on the inner side of the bending and the gaps 5c of the outer coiled part 5 are enlarged on the outer side of the bending.

At this time, the bending structure 1 smoothly bends by the inner coiled part 7 displacing outwardly in the diametral direction.

Namely, each coil 7b of the inner coiled part 7 is pushed inwardly in the diametral direction by reduction of the gaps 5c of the outer coiled part 5 on the inner side of the bending of the bending structure 1. According to this, the inner coiled part 7 as a whole is displaced outwardly in the diametral direction, and this displacement is allowed so that each coil 7b of the inner coiled part 7 enters into the enlarged gap 5c of the outer coiled part 5.

The bending structure 1, therefore, is the structure in which the compression is prevented in the axial direction whereas the flexibility is never hindered. As a result, the bending structure 1 is stabilized in the bending operation.

Further, when the bending structure 1 is bent, the gaps 5c of the outer coiled part 5 are reduced on the inner side of the bending and the gaps of the outer coiled part 5 are enlarged on the outer side of the bending as mentioned above. The size of the gaps 5c on the axis O is not changed by comparison with the straight state.

The bending structure 1, therefore, keeps the length of the axis O and the moving amount of the flexible member 3 passing on the axis O of the bending structure 1 constant at the time of not only the straight state, but the bending, thereby to ensure the stability of the operation of the flexible member 3.

Further, the bending structure 1 of the present embodiment brings the adjacent coils 5b of the outer coiled part 5 into contact with each other on the inner side of the bending when bending at the predetermined angle (FIG. 4).

In the bending structure 1, therefore, the length on the axis O starts to increase from when the coils 5b are brought into contact with each other. Accordingly, the bending at the predetermined angle or more is notified to an operator of the joint function part according to the change in the moving amount of the flexible member 3.

At the time of the bending operation of the bending structure 1, the inner coiled part 7 is prevented from being dropped off from the outer coiled part 5 by the flexible member 3.

Namely, the inner coiled part 7 as a whole is displaced outwardly in the diametral direction so that each coil 7b of the inner coiled part 7 enters into the enlarged gap 5c of the outer coiled part 5 at the time of the bending of the bending structure 1.

This displacement (movable length in which the inner coiled part 7 is movable in the diametral direction relatively to the axis O of the outer coiled part 5) is equal to or less than half of (the diameter of the outer coiled part–the diameter of the inner coiled part). In addition, the diameters mean the mean diameters D1 and D2 of the outer coiled part 5 and the inner coiled part 7. The diameters may be, however, outer diameters or inner diameters of the outer coiled part 5 and the inner coiled part 7.

Figures 5A, 5B:
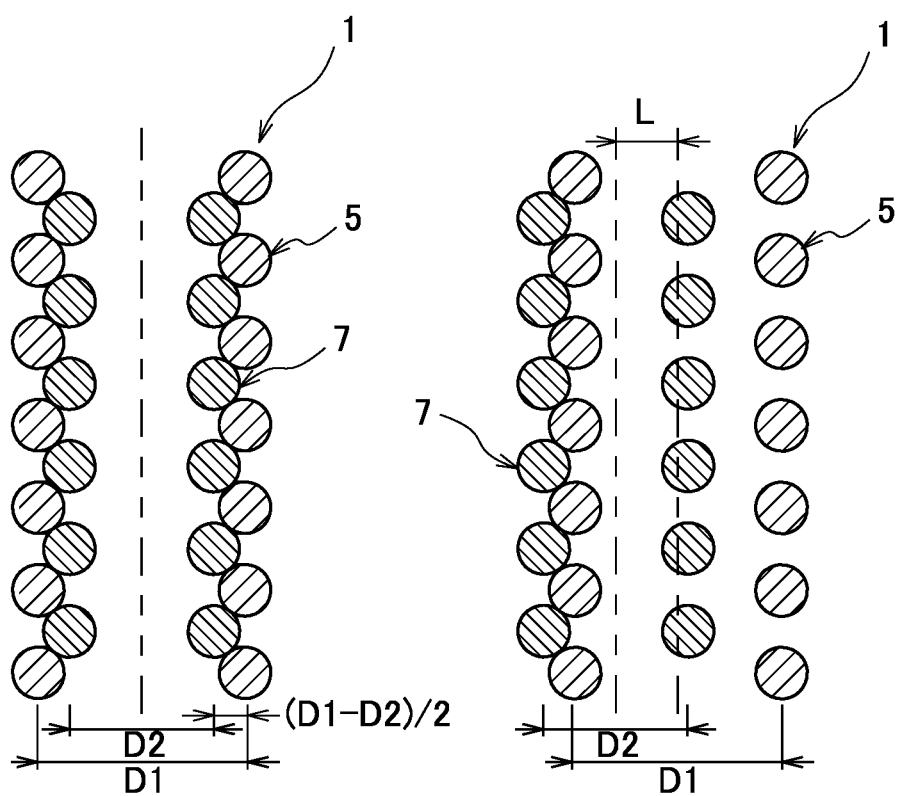

FIGS. 5A and 5B are schematic sectional views illustrating a drop-off of the inner coiled part 7 from the outer coiled part 5 in which 5A is a state before the drop-off and 5B is a state after the drop-off.

As illustrated in FIGS. 5A and 5B, if a moving amount L in the diametral direction of the inner coiled part 7 in the straight state exceeds (D1−D2)/2 being half of (the diameter of the outer coiled part 5–the diameter of the inner coiled part 7), the inner coiled part 7 gets over the outer coiled part 5 to be in a drop-off state. In addition, in FIG. 5, the moving amount L is indicated as a deviation amount between the axis of the inner coiled part 7 and the axis of the outer coiled part 5.

At the time of the bending of the bending structure 1, if the moving amount L of the inner coiled part 7 in the diametral direction exceeds (D1−D2)/2 being a half of (the diameter of the outer coiled part 5–the diameter of the inner coiled part 7), it results in causing the drop-off as illustrated in FIG. 5 when returning to the straight state. In the present embodiment, therefore, the movable length in which the inner coiled part 7 is movable in the diametral direction relatively to the axis O of the outer coiled part 5 is equal to or less than (D1−D2)/2 being half of (the diameter of the outer coiled part 5–the diameter of the inner coiled part 7).

The movable length is set by passing the flexible member 3 through the bending structure 1 in the present embodiment. In this way, in the present embodiment, the drop-off of the inner coiled part 7 from the outer coiled part 5 is prevented by the flexible member 3. The movable length may be, however, set by the setting of any one or both of the wire diameters d1 and d2 of the outer coiled part 5 and the inner coiled part 7 in a case that the bending structure 1 does not passes the flexible member 3 therethrough or a case that the diameter of the flexible member 3 is thin in a degree by which the aforementioned movable length cannot be set.

Figure 6A:
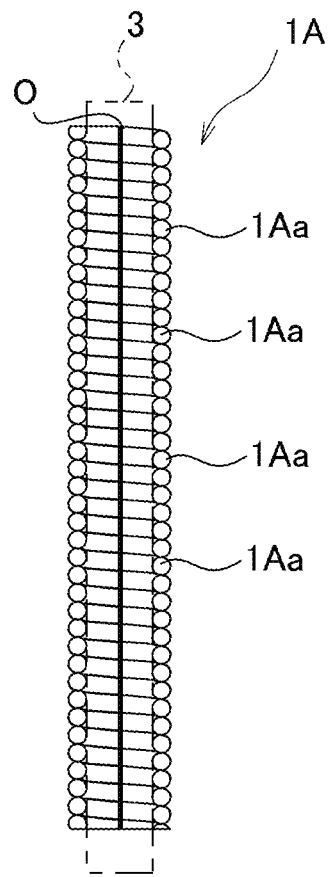
FIG. 6A is a sectional view illustrating a bending structure according to a comparative example.
Figure 6B:
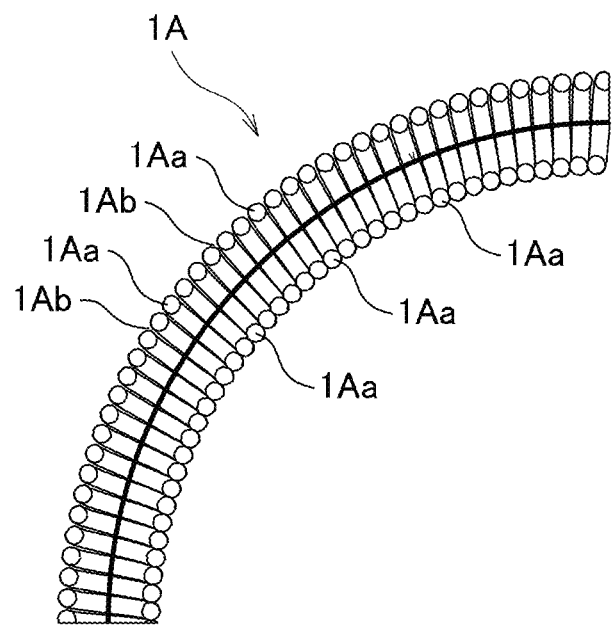
FIG. 6B is a sectional view illustrating a bending state of the bending structure according to the comparative example.

FIG. 6A is a sectional view illustrating a bending structure according to a comparative example, and FIG. 6B is a sectional view illustrating a bending state of the same.

The bending structure 1A according to the comparative example comprises of only a close contact spring, and is configured to be bendable and prevented from being compressed.

The bending structure 1A, at the time of bending, keeps a state in which coils 1Aa are in contact with each other on an inner side of the bending and forms gaps between the coils 1Aa on an outer side of the bending.

As this result, gaps 1Ab are also formed on a central portion of bending inner side and outer side of the bending structure 1A at the time of the bending. By the gaps 1Ab of the bending structure 1 A, a length of the axis O and the moving amount of the flexible member 3 passing on the axis O are increased.

Accordingly, the comparative example is one which does not ensure stability of operation of the flexible member 3 when guiding the flexible member 3 unlike the embodiment 1.

As mentioned above, the bending structure 1 of the present embodiment is the bending structure which movably passes the flexible member 3 therethrough in the axial direction and is bendable as well as the flexible member 3. The bending structure is provided with the outer coiled part 5 formed of the wire 5a which is wound in the coiled shape to have the plurality of coils 5b in the axial direction, and the inner coiled part 7 formed of the wire 7a which is wound in the coiled shape to have the plurality of coils 7b in the axial direction and arranged in the outer coiled part 5.

The outer coiled part 5 has the plurality of the gaps 5c to distance the adjacent coils 5b, and the coils 7b of the inner coiled part 7 are provided so as to correspond to the gaps 5c of the outer coiled part 5 and fit between the adjacent coils 5b while being in contact with the adjacent coils 5b of the outer coiled part 5.

The bending structure 1, therefore, is formed by arranging the inner coiled part 7 into the outer coiled par 5, so that the structure is simplified.

Further, the bending structure 1 prevents, by the coils 7b of the inner coiled part 7, the gaps 5c of the outer coiled part 5 from being compressed to be prevented from being compressed as whole even if the compressive force acts in the axial direction. Accordingly, the bending structure 1 ensures the rigidity in the axial direction in a degree not to cause the joint function part to be compressed.

Further, the inner coiled part 7 is displaced toward the outer side of the bending while the gaps 5c of the outer coiled part 5 are reduced on the inner side of the bending at the time of the bending, and the gaps of the outer coiled part 5 are enlarged on the outer side of the bending to allow the displacement of the inner coiled part 7, thereby to ensure sufficient flexibility to bend as well as the joint function part even while the rigidity in the axial direction is ensured.

As a result, the bending structure 1 enables its structure to be simplified while stabilizing the bending operation, so that it ensures stability of operation of a device such as a robot, manipulator, or actuator having the joint function part.

Further, in the bending structure 1 of the present embodiment, the gaps 5c of the outer coiled part 5 are reduced on the inner side of the bending and the gaps 5c of the outer coiled part 5 are enlarged on the outer side of the bending. The length of the axis O of the outer coiled part 5 is not changed by comparison with the straight state, and the moving amount of the flexible member 3 is certainly kept constant.

Accordingly, stability of the operation of the flexible member 3 is ensured and therefore the stability of operation of the device having the joint function part is further ensured.

Further, in the present embodiment, the movable length (displacement amount) in which the inner coiled part 7 is movable in the diametral direction relatively to the axis O of the outer coiled part 5 is equal to or less than half of (the diameter of the outer coiled part−the diameter of the inner coiled part). The inner coiled part 7, therefore, is prevented from being dropped off from the outer coiled part 5.

Furthermore, in the present embodiment, the flexible member 3 as the restricting member restricts the movement of the inner coiled part 7 so that the movable length is equal to or less than half of (the diameter of the outer coiled part−the diameter of the inner coiled part). The inner coiled part 7 is, therefore, easily prevented from being dropped off without changing shapes of the inner coiled part 7 and the outer coiled part 5.

The bending structure 1 movably passes the flexible member 3 therethrough in the axial direction and is bendable together with the flexible member 3. The inner coiled part 7 is, therefore, prevented from being dropped off by using the flexible member 3 in the aspect to guide the flexible member 3.

In the present embodiment, the outer coiled part 5 has the gaps 5c in the respective interspaces between the adjacent coils 5b in the axial direction, so that the bending structure 1 is bent smoothly.

In the present embodiment, the inner coiled part 7 and the outer coiled part 5 are formed separately and the inner coiled part 7 is screwed into the outer coiled part 5, so that the assembly is easily performed. Further, characteristics of the bending structure 1 are easily varied by varying characteristics of any one or both of the inner coiled part 7 and the outer coiled part 5.

Further, since the bending structure 1 of the present embodiment brings the adjacent coils 5b of the outer coiled part 5 into contact with each other on the inner side of the bending when bending at the predetermined angle, the bending at the predetermined angle or more is notified to an operator of the joint function part according to the change in the moving amount of the flexible member 3.

Figure 7:
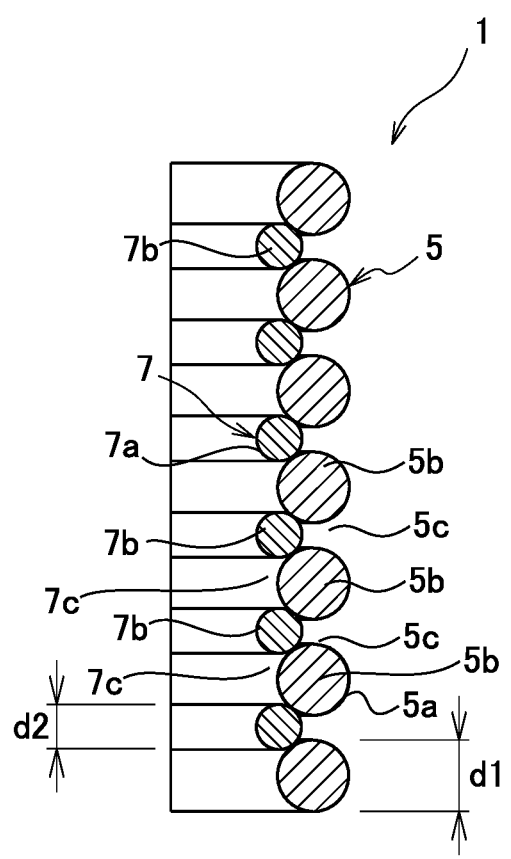
FIG. 7 is an enlarged sectional view illustrating a part of a bending structure according to an embodiment 2 of the present invention.

FIG. 7 is an enlarged sectional view illustrating a part of a bending structure according to the embodiment 2. In addition, components in the embodiment 2 corresponding to in the embodiment 1 are represented with the same reference numerals to eliminate duplicate explanation.

A bending structure 1 of the embodiment 2 is one in which a wire diameter d1 of a wire 5a of an outer coiled part 5 is different from a wire diameter d2 of a wire 7a of an inner coiled part 7. In the embodiment 2, the wire diameter d1 of the outer coiled part 5 is set greater than the wire diameter d2 of the inner coiled part 7. It should be noted that the wire diameter d1 of the outer coiled part 5 may be smaller than the wire diameter d2 of the inner coiled part 7.

The bending structure 1 provides the same effect as the embodiment 1 even in the case that the wire diameter d1 of the outer coiled part 5 is different from the wire diameter d2 of the inner coiled part 7 in this way. Further, a free length and characteristics of the bending structure 1 are adjusted by differing the wire diameter d2 and the wire diameter d1 from each other.

Figure 8:
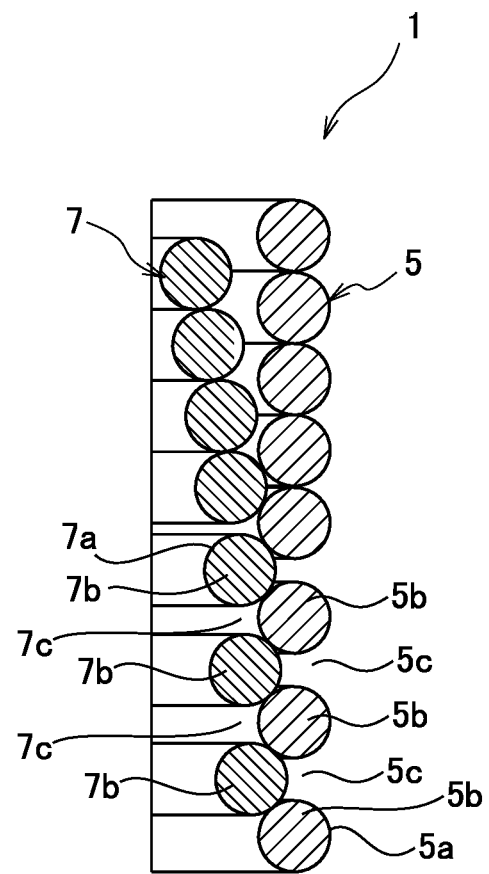
FIG. 8 is an enlarged sectional view illustrating a part of a bending structure according to an embodiment 3 of the present invention.

FIG. 8 is an enlarged sectional view illustrating a part of a bending structure according to the embodiment 3. In addition, components in the embodiment 3 corresponding to in the embodiment 1 are represented with the same reference numerals to eliminate duplicate explanation.

A bending structure 1 of the embodiment 3 fits coils 7b of an inner coiled part 7 between adjacent coils 5b while be in contact with the adjacent coils 5b of an outer coiled part 5 in part of the outer coiled part 5 in an axial direction.

Namely, the inner coiled part 7 is formed so that a mean diameter D2 (see FIG. 1) becomes gradually small in the axial direction. According to this, the inner coiled part 7 fits between the adjacent coils 5b of the outer coiled part 5 only in the part of the outer coiled part 5 in the axial direction as mentioned above.

In addition, in the present embodiment, the inner coiled part 7 and the outer coiled part 5 are respective close contact springs and gaps 5c of the outer coiled part 5 are reduced as reduction of the mean diameter D2 of the inner coiled part 7.

Even this structure provides the same effect as the embodiment 1. Additionally, the present embodiment fits the coils 7b of the inner coiled part 7 between the adjacent coils 5b of the outer coiled part 5 only in the part of the outer coiled part 5 in the axil direction, thereby to adjust a free length and characteristics of the bending structure 1.

Figure 9:
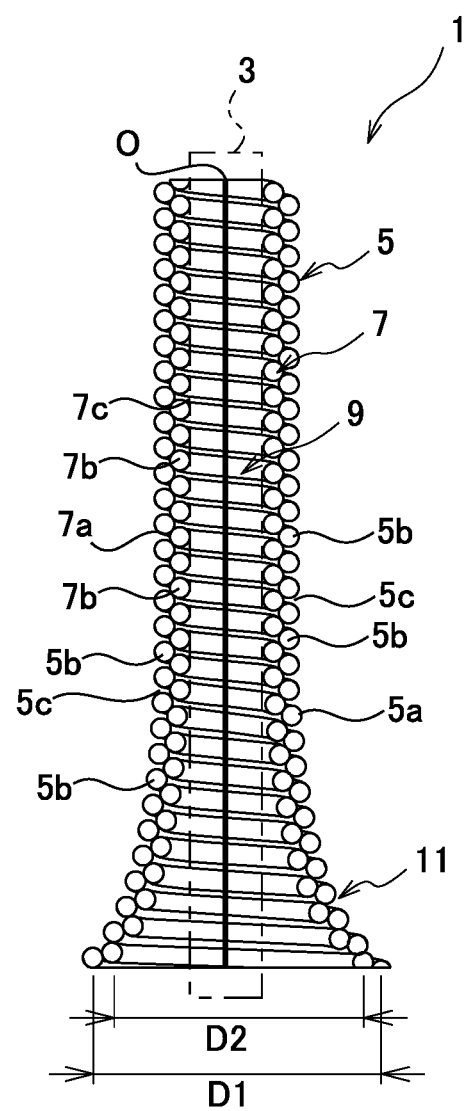
FIG. 9 is a sectional view illustrating a bending structure according to an embodiment 4 of the present invention.

FIG. 9 is a sectional view illustrating a bending structure according to the embodiment 4. In addition, components in the embodiment 4 corresponding to in the embodiment 1 are represented with the same reference numerals to eliminate duplicate explanation.

A bending structure 1 of the embodiment 4 is provided with an enlarged diameter portion 11 gradually increasing in diameter in part in an axial direction. In the present embodiment, the enlarged diameter portion 11 is provided at one end of the bending structure 1 in the axial direction. The enlarged diameter portion 11 may be provided in the middle of or at the other end of the bending structure 1 in the axial direction.

At the enlarged diameter portion 11, both mean diameters D1 and D2 of an outer coiled part 5 and an inner coiled part 7 are enlarged gradually, and it keeps a state in which coils 7b of the inner coiled part 7 fit between coils 5b while be in contact with the adjacent coils 5b of the outer coiled part 5.

Even this structure provides the same effect as the embodiment 1. Further, the enlarged diameter portion 11 adjusts characteristics of the bending structure 1.

Figure 10:
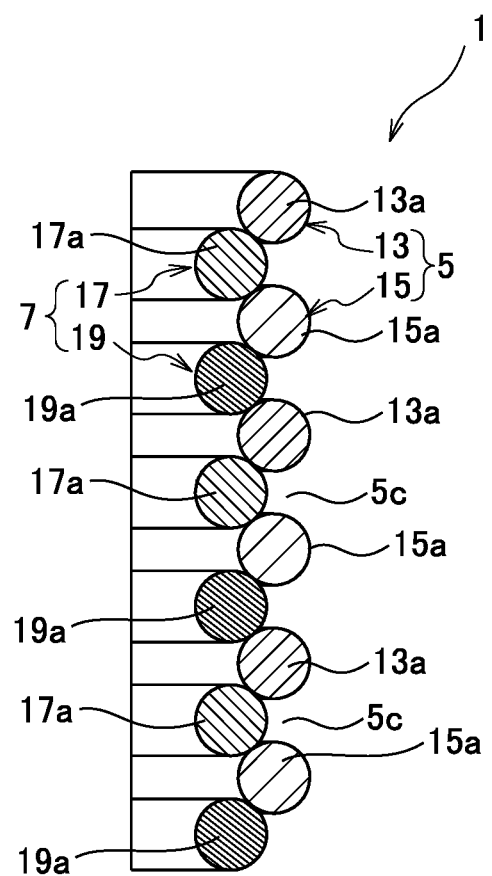
FIG. 10 is an enlarged sectional view illustrating a part of a bending structure according to an embodiment 5 of the present invention.

FIG. 10 is an enlarged sectional view illustrating a part of a bending structure according to the embodiment 5. In addition, components in the embodiment 5 corresponding to in the embodiment 1 are represented with the same reference numerals to eliminate duplicate explanation.

A bending structure 1 of the embodiment 5 is one in which an outer coiled part 5 and an inner coiled part 7 are respectively configured by two coil parts. In particular, the outer coiled part 5 is composed of a first outer coiled part 13 and a second outer coiled part 15 and the inner coiled part 7 is composed of a first inner coiled part 17 and a second inner coiled part 19.

In the first outer coiled part 13 and the second outer coiled part 15, coils 13a, 15a are alternately arranged in an axial direction, and in also the first inner coiled part 17 and the second inner coiled part 19, coils 17a, 19a are alternately arranged in the axial direction.

Namely, in the outer coiled part 5, the coils 13a, 15a of the first outer coiled part 13 and the second outer coiled part 15 are adjacent to each other in the axial direction to form gaps 5c between those adjacent coils 13a, 15a.

The coils 17a of the first inner coiled part 17 and the coils 19a of the second inner coiled part 19 of the inner coiled part 7 respectively fit between the coils 13a, 15a while being in contact with the coils 13a, 15a of the first outer coiled part 13 and the second outer coiled part 15.

Even this structure provides the same effect as the embodiment 1 and adjusts a free length and characteristics of the bending structure 1.

It should be noted that the number of coiled parts composing the outer coiled part 5 and the inner coiled part 7 may be varied. Further, only one of the outer coiled part 5 and the inner coiled part 7 may be composed of a plurality of coiled parts.

Figure 11:
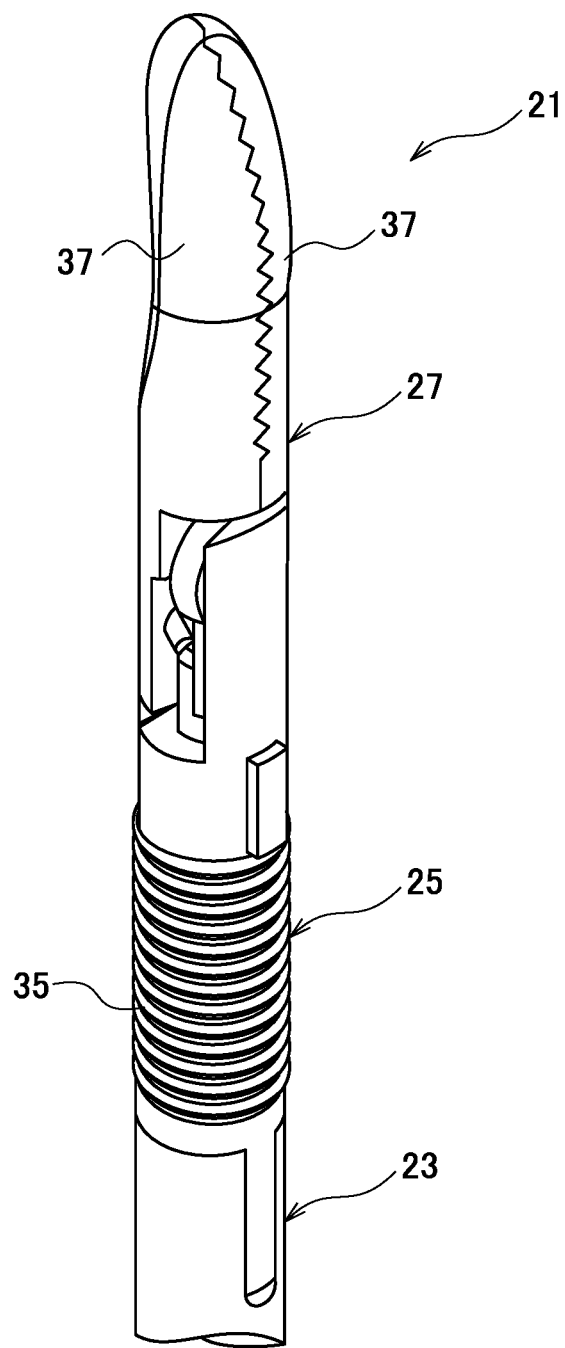
FIG. 11 is a perspective view illustrating a part of robot forceps according to an embodiment 5 of the present invention.
Figure 12:
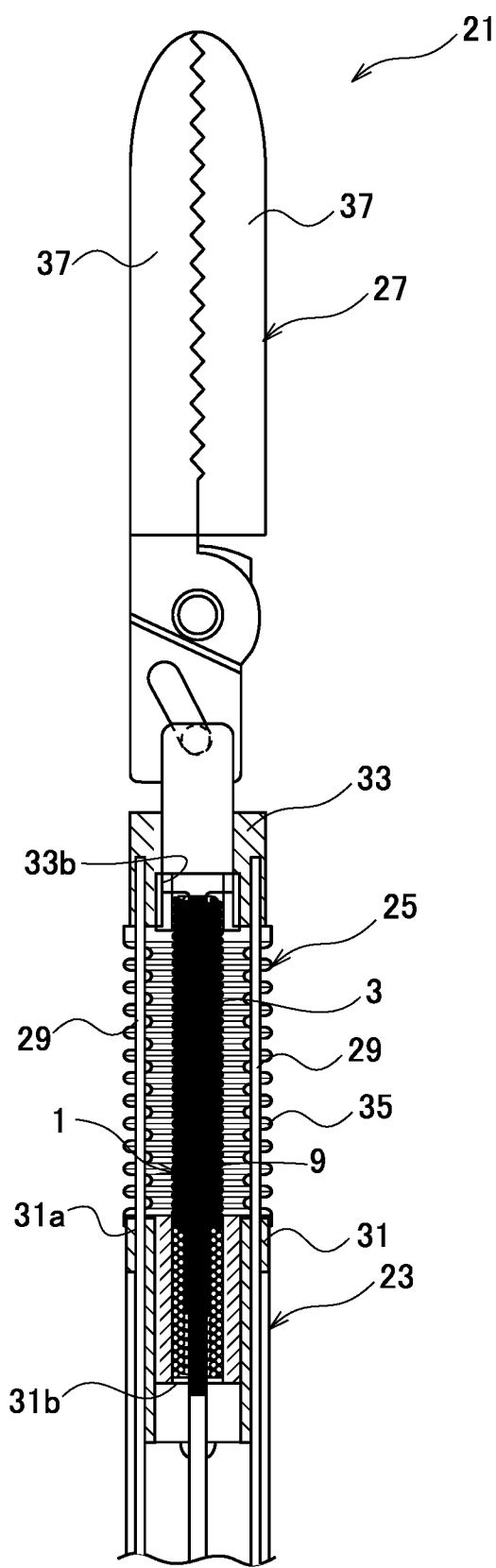
FIG. 12 is a sectional view of the robot forceps of FIG. 11.
Figure 13:
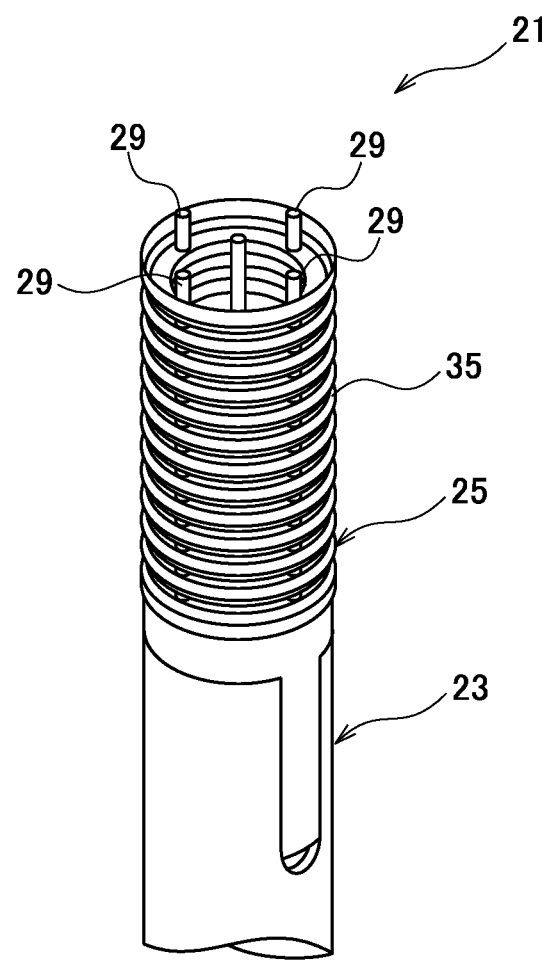
FIG. 13 is a perspective view illustrating a bendable part of the robot forceps of FIG. 11.
Figure 14:
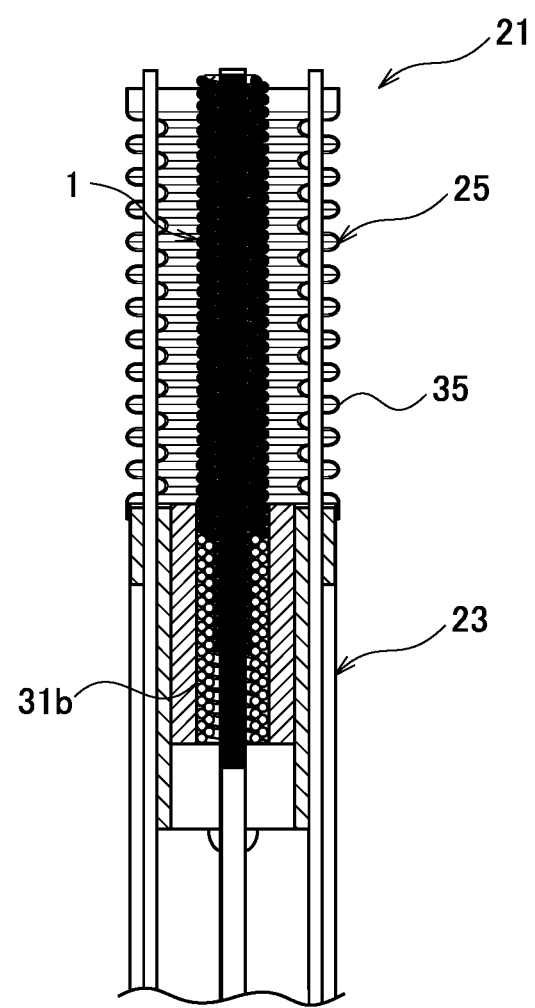
FIG. 14 is a sectional view of the bendable part of FIG. 13.

FIG. 11 is a perspective view illustrating a part of robot forceps to which a bending structure is applied according to the embodiment 6 of the present invention, FIG. 12 is a sectional view of the same, FIG. 13 is a perspective view illustrating a joint function part of the robot forceps of FIG. 11, and FIG. 14 is a sectional view of the same. In addition, components in the embodiment 6 corresponding to in the embodiment 1 are represented with the same reference numerals to eliminate duplicate explanation.

Robot forceps 21 of the present embodiment is one which forms a front end of a robot arm of a surgical robot as a medical manipulator.

In addition, the robot forceps 21 are an example of a device having a joint function part. The device having a joint function part is not limited to the medical manipulator as mentioned above. Namely, the device having the joint function part is not particularly limited, but a robot in the other field, every kind of manipulators, actuators or the like as long as it has the joint function part performing bending operation and moves a flexible member 3 in an axial direction to perform operation or the like. Further, in a case of a medical manipulator, an endoscope camera, manual forceps and the like that are not attached to surgical robots are included.

The robot forceps 21 of the present embodiment is composed of a shaft 23, a joint function part 25, and a holding unit 27 as an end effector for surgical operation.

The shaft 23 is formed into, for example, a cylindrical shape. Passed in the shaft 23 are driving wires 29 to drive the joint function part 25 and a flexible member 3 being a push-pull cable to drive the holding unit 27. On a front end side of the shaft 23, the holding unit 27 is provided through the joint function part 25.

The joint function part 25 is provided with a base part 31, a movable part 33, a flexible tube 35, and a bending structure 1.

The base part 31 is a cylinder body formed of resin, metal or the like, and is attached at the front end of the shaft 23. Through the base part 31, the driving wires 29 pass via through-holes 31a in the axial direction and the flexible member 3 passes via an insertion hole 31b on an axial center portion.

The movable part 33 is a cylinder body formed of resin, metal or the like, and is attached to the holding unit 27 explained later. To the movable part 33, front end portions of the driving wires 29 are fixed. Accordingly, the movable part 33 is displaced with respect to the base part 31 by operation of the driving wires 29 to orient the holding unit 27 toward a desired direction. An axial center portion of the movable part 33 is provided with an insertion hole 33b to pass the flexible member 3 therethrough.

The flexible tube 35 is interposed between the base part 31 and the movable part 33 and is bent according to the displacement of the movable part 33 relative to the base part 31. The flexible tube 35 passes the driving wires 29 and the flexible member 3 therethrough in the axial direction.

The flexible tube 35 of the present embodiment is configured by a bellows formed of a tube body having a wave sectional shape. The flexible tube 35 may use, however, a coil spring, a tube body or the like, and is not particularly limited as long as it has a flexible tube shape.

The bending structure 1 is the same as of the embodiment 1. The bending structure 1 is arranged along the axial center portion of the flexible tube 35 and is provided between the base part 31 and the movable part 33. In addition, the bending structure 1 of any one of the embodiments 2-5 may be applied to the joint function part 25.

The bending structure 1 passes the flexible member 3 through the passing portion 9, in this state both ends of which are respectively attached to the insertion holes 31*b* and 33*b* of the base part 31 and the movable part 33. With this, the bending structure 1 supports the movable part 33 with respect to the base part 31 so as not to be movable in the axial direction and is bendable as well as the flexible member 3 according to the displacement of the movable part 33 relative to the base part 31.

The holding unit 27 has a pair of holding parts 37 openably pivotally supported with respect to the movable part 33 of the joint function part 25. The holding unit 27 is connected to the flexible member 3 passing through the joint function part 25 and is configured to open and close the holding parts 37 by axial movement (reciprocation movement) of the flexible member 3. It should be noted that the end effector is not limited to the holding unit 27 and may be, for example, scissors, a holding retractor, a needle driver or the like.

In the robot forceps 21 having the structure, an operator such as a doctor reciprocatingly operates the flexible member 3, thereby to cause the holding parts 37 of the holding unit 27 to perform opening/closing operation.

Further, the operator pulls any one or some of the driving wires 29 to bend the joint function part 25, thereby to cause the holding unit 27 to orient relatively to the shaft 23 toward a desired direction. In this state, if the flexible member 3 is reciprocated, the holding parts 37 of the holding unit 27 is caused to perform the opening/closing operation.

The opening/closing operation is stabilized and accurately performed because the moving amount of the flexible member 3 is constant as mentioned in the embodiment 1.

Additionally, the present embodiment provides the same effect as the embodiment 1.

The invention claimed is:

1. A bending structure being bendable with respect to an axial direction, comprising:
   an outer coiled part formed of a wire which is wound in a coiled shape to have a plurality of coils in the axial direction; and
   an inner coiled part formed of a wire which is wound in a coiled shape to have a plurality of coils in the axial direction and arranged in the outer coiled part; and
   a flexible member extending inside the inner coiled part in the axial direction and movable in the axial direction to conduct operation, wherein
   the outer coiled part has a plurality of gaps to distance adjacent coils in the axial direction,
   the coils of the inner coiled part are provided so as to correspond to the gaps of the outer coiled part and fit between the adjacent coils while being in contact with the adjacent coils of the outer coiled part,
   the inner coiled part has a passing portion defined by an inner circumference of the inner coiled part, the inner circumference directly facing an outer circumference of the flexible member in a diametral direction, and the passing portion movably passing and guiding the flexible member in the axial direction so that the bending structure movably passes the flexible member through the passing portion in the axial direction and is bendable as well as the flexible member, and
   the flexible member has flexibility that allows the flexible member to axially move in the passing portion in a bending state of the inner and the outer coiled parts of the bending structure while keeping a bending posture of the inner and the outer coiled parts in said bending state without change.

2. The bending structure according to claim 1, wherein the outer coiled part has the gaps in respective interspaces of the adjacent coils in the axial direction.

3. The bending structure according to claim 1, wherein a movable length in which the inner coiled part is movable in a diametral direction relative to an axis of the outer coiled part is equal to or less than half of a diameter of the outer coiled part minus a diameter of the inner coiled part.

4. The bending structure according to claim 1, further comprising:
   a restricting member to restrict movement of the inner coiled part so that a movable length is equal to or less than half of a diameter of the outer coiled part minus a diameter of the inner coiled part.

5. The bending structure according to claim 4, wherein the restricting member is the flexible member.

6. The bending structure according to claim 1, wherein the inner coiled part and the outer coiled part are formed separately and the inner coiled part is screwed into the outer coiled part.

7. The bending structure according to claim 1, wherein the outer coiled part brings the adjacent coils into contact with each other when bending at a predetermined angle.

8. A joint function part to which the bending structure according to claim 1 is applied, comprising:
   a base part and a movable part configured to displace relative to the base part, wherein
   the bending structure is provided between the base part and the movable part to bend according to displacement of the movable part relative to the base part.

9. The joint function part according to claim 8, further comprising:
   a flexible tube being interposed between the base part and the movable part and being extendable and compressible in the axial direction, wherein
   the bending structure is arranged along an axial center portion of the flexible tube in the axial direction.

10. The bending structure according to claim 8, wherein the outer coiled part has the gaps in respective interspaces of the adjacent coils in the axial direction.

11. The bending structure according to claim 8, wherein a movable length in which the inner coiled part is movable in a diametral direction relative to an axis of the outer coiled part is equal to or less than half of a diameter of the outer coiled part minus a diameter of the inner coiled part.

12. The bending structure according to claim 8, further comprising:
   a restricting member to restrict movement of the inner coiled part so that the movable length is equal to or less than half of a diameter of the outer coiled part minus a diameter of the inner coiled part.

13. The bending structure according to claim 12, wherein the restricting member is the flexible member.

14. The bending structure according to claim 8, wherein the inner coiled part and the outer coiled part are formed separately and the inner coiled part is screwed into the outer coiled part.

15. The bending structure according to claim 8, wherein the outer coiled part brings the adjacent coils into contact with each other when bending at a predetermined angle.

* * * * *